United States Patent [19]

Eimers et al.

[11] 4,324,934
[45] Apr. 13, 1982

[54] HYDROCARBON, A PROCESS FOR ITS PRODUCTION AND ITS USE AS A REACTIVE THINNER FOR AIR-DRYING LACQUERS

[75] Inventors: Erich Eimers; Rolf Dhein, both of Krefeld, Fed. Rep. of Germany

[73] Assignee: Bayer Aktiengesellschaft, Leverkusen, Fed. Rep. of Germany

[21] Appl. No.: 223,567

[22] Filed: Jan. 9, 1981

[30] Foreign Application Priority Data

Jan. 18, 1980 [DE] Fed. Rep. of Germany ....... 3001739

[51] Int. Cl.³ .......................... C09D 7/06; C07C 2/52; C07C 13/605; C08K 5/01
[52] U.S. Cl. ..................................... 585/21; 583/360; 525/44; 524/457
[58] Field of Search .................... 585/23, 22, 21, 318, 585/360, 316; 106/191; 260/33.6

[56] References Cited

U.S. PATENT DOCUMENTS

| 2,582,434 | 1/1952 | Hoffman et al. | 585/318 |
| 3,496,129 | 2/1970 | Wismer et al. | 585/21 |

FOREIGN PATENT DOCUMENTS

| 59251 | 2/1970 | Poland | 585/360 |
| 282648 | 6/1969 | U.S.S.R. | 585/360 |

OTHER PUBLICATIONS

A. Takahashe et al., Chem. Comm. 1970, No. 22, 1473.

*Primary Examiner*—Delbert E. Gantz
*Assistant Examiner*—Helane E. Maull
*Attorney, Agent, or Firm*—Connolly and Hutz

[57] ABSTRACT

The 1:1-adduct of 1.3-butadiene and dicyclopentadiene is an excellent reactive thinner for air-drying lacquers.

8 Claims, No Drawings

HYDROCARBON, A PROCESS FOR ITS PRODUCTION AND ITS USE AS A REACTIVE THINNER FOR AIR-DRYING LACQUERS

This invention relates to an adduct of 1,3-butadiene and dicyclopentadiene, to a process for producing this adduct by homogeneous catalysis and to its use as a reactive thinner for air-drying lacquers.

Reactive thinners are low-viscosity substances which are used to thin resin-like binders and, hence, provide the lacquer with the viscosity required for its application. They contain functional groups capable of copolymerisation or co-condensation with the lacquer resin and, during the hardening process, they become part of the hardened lacquer film to a predominant extent, depending in each case on their volatility.

Accordingly, reactive thinners for air-drying lacquers have to contain function groups, for example activated, preferably conjugated, double bonds which are capable of participating in the crosslinking reaction induced by the oxygen in the air. Alloocimen, one such reactive diluent, has already been on the market for some time, but is only of limited use on account of its intensive unpleasant odour, even in heavily diluted form, and its relatively high volatility.

Adducts of 1,3-butadiene with dicyclopentadiene (DCP) are known. Thus, it is known that, given a large excess of butadiene, 2 molecules of butadiene undergo addition with 1 molecule of DCP in the presence of organometallic complex compounds of zero-valent nickel and that a new anellated ring is formed by ring closure of the 2 butadienyl radicals. The mixed oligomers formed contain only isolated double bonds and, even at relatively low temperatures, undergo rearrangement in the manner of Cope's rearrangement. In addition, the compounds are crystalline at room temperature; cf. Rolf-Volker Meyer, "Mischoligomerisation von Butadien mit gespannten Olefinen an Nickelkatalysatoren", Diss. Bochum, 1973.

Butadiene may be reacted with other compounds by homogeneous catalysis so that its system of conjugated double bonds intact, but only with compounds of the type which contain particularly activated double bonds. Thus, it is possible by heating equimolar quantities of 1,3-butadiene and norbornadiene, which is a highly activated olefin by virtue of extreme ring tension, in the presence of low-valency cobalt complexes in an autoclave to obtain a 1:1-adduct containing a pair of conjugated double bonds. The main isomer accumulates in a yield of about 50% (A. Takahashe et al., Chem. Comm. 1970, No. 22, 1473). Our own tests have shown that, where this adduct is used as a reactive thinner, a comparatively small proportion remains in the hardened lacquer film on account of its high volatility.

It has now been found that DCP may also be reacted with 1,3-butadiene to form a 1:1-adduct containing conjugated double bonds, in surprisingly high yields, which was not foreseeable on account of the poor reactivity of DCP. However, the reaction only proceeds satisfactorily under conditions which differ significantly from those applied in the production of the adducts previously mentioned.

In contrast to the processes mentioned above, the principle of this production process is to keep the concentration of the butadiene as low as possible throughout the entire reaction. This may be done by introducing at least the major proportion of the gaseous 1,3-butadiene into a solution of a catalyst in heated DCP over a prolonged period and at most as quickly as it is consumed. The yield amounts to 90%, based on the DCP reacted. The codimer obtained may readily be separated off from the reaction mixture by distillation.

The molecular weight of the codimer, as determined by mass spectrometry, amounts to 186 which corresponds to the expected value for a 1:1-adduct. The IR-spectrum shows one isolated double bond and two conjugated double bonds. A Diels-Alder adduct is formed in an exothermic reaction with maleic acid anhydride. On the strength of these data, the following structures

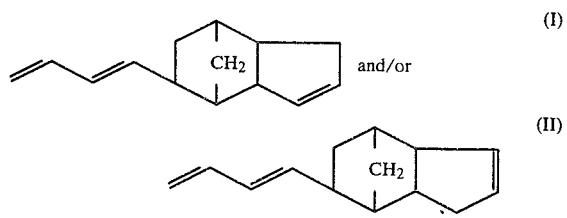

are attributed to the codimer obtained.

Accordingly, the present invention provides 1:1-codimers of DCP and 1,3-butadiene having a molecular weight of 186.

The present invention also provides a process for the production of 1:1-codimers of DCP and 1,3-butadiene which is characterised in that gaseous 1,3-butadiene is reacted with DCP at 40° to 100° C. and preferably at 50° to 70° C. in the presence of an organocobalt complex compound, most of the 1,3-butadiene being added at most at a rate commensurate with its reaction velocity.

In one preferred procedure, the 1,3-butadiene is added in a quantity from 0.05 to 0.5 mole/h per mole of DCP. The molar ratio of butadiene to DCP is preferably from 0.1 to 2 and more particularly from $\frac{1}{3}$ to 1.

The present invention also relates to the use of the codimers according to the invention as reactive thinners for air-drying lacquers.

Preferred catalysts for the process according to the invention are the organic complex compounds of zerovalent and monovalent cobalt, such as for example cyclooctenylcyclooctadienyl-cobalt, 3-methyl-heptadienyl-cobalt, bis-(cyclooctadiene)-ethyl-cobalt, tris-allyl-cobalt, tetrakistrisphenyl-phosphine-cobalt, cobalt-bis-1,2-(diphenyl-phosphine-ethane)-hydride, cobalt-bis-1,2-diphenyl-phosphine methane and the like, i.e. complex compounds of the type described, for example, in German Auslegeschrift No. 1,191,375 or in Internat. Congress Pure Appl. Chem. 6,265 et seq (1971). The catalysts are generally used in a quantity of from 1 to 15 mMoles/mole of butadiene.

The catalysts may also be prepared in situ in known manner by reacting salts of cobalt, for example, cobalt acetate, chloride or acetyl acetonate, with strong reducing agents, for example sodium borohydride, sodium amalgam, potassium, sodium, aluminium diethyl chloride, oxyalkyl aluminium dialkyl, aluminium triethyl etc., in the presence of complex-forming ligands, for example butadiene, allyl compounds, cyclooctadiene, cyclopentadiene, triphenyl phosphine, triphenyl stibine, pyridine, in DCP introduced before-hand within the reaction mixture.

The process according to the invention may be carried out either in the presence or absence of inert solvents. Preferred solvents are aromatic hydrocarbons, such as benzene, toluene, cycloaliphatic hydrocarbons, such cyclohexane, aliphatic and cycloaliphatic ethers, such as dimethyl ether, diethyl ether, tetrahydrofuran, dioxane, diethylene glycol, glycol-1,2-dimethyl ether, esters of carboxylic acids containing from 2 to 4 carbon atoms and alcohols containing from 1 to 4 carbon atoms, such as ethyl acetate, butyl acetate and glyol bis-acetate.

The process according to the invention should be carried out in the absence of oxygen and moisture; cf. for example Methoden der organischen Chemie (Houben-Weyl), Vol. I/2, 4th Edition, 326–390, Georg Thieme Verlag, Stuttgart 1959.

For its use as a reactive thinner, the codimer according to the invention may be employed in pure or enriched form. Thus it is possible, for example to use those fractions of the reaction mixture, in which the codimer is present in a concentration of at least 60% by weight.

Preferred air-drying binders for which the codimers according to the invention may be advantageously used as reactive thinners are alkyd resins, i.e. fatty-acid-modified and oil-modified polyesters of the type described for example by D. H. Solomon in "The Chemistry of Organic Film-Formers", pages 75 to 101, John Wiley and Sons Inc., New York, 1967. The alkyl resins are air-drying when they contain residues of polyunsaturated fatty acids, for example linoleic acid, linoleic acid, eleostearic acid, ricinene acid and the like, in co-condensed form.

The reactive thinner may also be used in combination with standard lacquer solvents such as, for example, mineral spirit, xylene, naphtha diacetone alcohol, etc. From 10 to 100% by weight of the lacquer solvent should consist of the codimer according to the invention.

In addition to the binder, the reactive thinner and optionally, inert solvents, the air-drying lacquers may of course also contain inorganic and organic pigments, anti-skinning agents, for example, phenols or oximes, and levelling agents for example, siloxane compounds. To accelerate the air-drying process, they may contain active heavy metal salts, for example octoates or naphthanates of lead, manganese, cobalt, cerium or zirconium, or mixtures thereof.

The solid resin content of the air-drying lacquers may vary within wide limits, but preferably amount to between 20 and 80% by weight.

The high compatibility of the codimer according to the invention with air-drying lacquers is reflected in the relatively low viscosity of solutions in codimer compared with solutions in mineral spirit. Accordingly, the codimer according to the invention is eminently suitable for the production of lacquers of high resin content. In their case, the codimer is irreversibly fixed in the lacquer film during the drying process.

The codimer according to the invention is also suitable for use as a copolymerisation component for thermoplasts and elastomers.

The percentages and parts quoted in the following Examples represent percentages and parts by weight.

EXAMPLES

EXAMPLE 1

3.4 g of cobalt acetyl acetonate are dissolved in 270 g of DCP in a medium free from air and moisture (inert gas argon). 13 g of gaseous 1,3-butadiene are condensed in this solution under a slight excess pressure (approximately 15 Torr) at −20° C. 3.8 g of triethyl aluminium are then introduced by pipette, after which the mixture is left standing for 30 minutes at the aboveindicated temperature and is subsequently heated to 50° C. After reaching this temperature, 95 g of 1,3-butadiene are introduced over a period of 6 h (0.14 mole/h per mole of DCP).

On completion of the reaction, the reaction mixture weighs 310 g, corresponding to a butadiene conversion of the order of 30%. The catalyst is destroyed by the addition of a little methanol. The reaction mixture is then fractionated.

Result of fractionation:
Fraction 1: 174 g 36°–60° C./0.1 Torr (unreacted DCP)
Fraction 2: 105 g 60°–110° C./0.1 Torr
Distillation residue: 31 g (brown, viscous oil)
Fraction 2 is again distilled:
Fraction 3: 54.5 g 55°–70° C./0.1 Torr
Fraction 4: 39.2 g 70°–80° C./0.1 Torr
Residue 11 g Both fractions are analysed by gas chromatography.
Conditions:
Column: 4 m stainless steel tube ⌀ ⅛ mm
Filling: 4% OV 101 on Chromosorb G-AW-DMCS, carrier gas: helium
Flow rate: 25 ml/min, detector current: 150 mA
Temperatures:
Injector: 300° C., detector: 300° C., furnace: 100°–320° C., 8° C./min.,
Injection volume: 0.002 ml
Advance of recording paper: 0.5 cm/min.

|  | Result |  |
| --- | --- | --- |
|  | DCP | Codimer |
| Fraction 3: | 87.6% | 1% |
| Fraction 4: | 1% | 88.5% |

Fine fractionation of the codimer peak by gas chromatography shows a split into 3 components, presumably stereo isomers. All three components show a molecular weight of 186 in the mass spectrum. In recording the IR-spectrum of a codimer fraction enriched by distillation to a purity of 95% (cf. Example 2), the following characteristic bands appear:

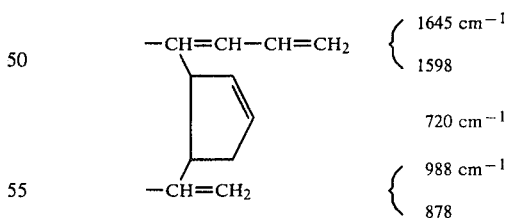

Yield: 51%, based on the DCP reacted.

EXAMPLE 2

Following the procedure of Example 1, 132 g of DCP are heated to 60° C. in argon with 3 g of cyclooctenyl-cyclooctadienylcobalt. 54 g of 1,3-butadiene are then introduced over a period of 6 hours (at a rate of 0.167 mole/h per mole of DCP). On completion of the addition, 185 g of a brown-coloured oil are left, corresponding to a butadiene conversion of 92.6%. 103 g of unreacted DCP are recovered during working up of the crude product by distillation in the presence of 0.1 g of phenothiazine. After redistillation of the main fraction, 27 g of adduct with a purity of 95% as determined by gas chromatography are obtained at a head temperature of 70° to 78° C./0.1 Torr. Yield, based on the DCP reacted: 62.7%.

EXAMPLE 3

Following the procedure of Example 1, 108 g of 1,3-butadiene are introduced over a period of 6 hours (at a rate of 0.095 mole/h per mole of DCP) into 462 g of dicyclopentadiene containing 5.5 g of cyclooctadienyl-cobalt. The temperature during introduction of the 1,3-butadiene is 65° C. The crude product is obtained in a quantity of 549 g.

Working up by distillation in the same way as in the preceding Examples gives 408 g of unreacted DCP and 77.2 g of codimer fraction with a purity of around 90%. Yield: 91.4%, based on the DCP reacted.

EXAMPLE 4

Use of the codimer as a reactive thinner 33 parts of a 70% solution in white spirit of a standard commercial alkyd resin containing approximately 48% of soya oil fatty acids (Alkydal ® F 48, a product of Bayer AG) are dissolved with 10 parts of codimer (purity 88%). 2.23 parts of a siccative solution are added to this solution. The composition of the siccative solution was: 15% of cobalt octoate solution (metal content 6%), 62.7% of lead octoate solution (metal content 24%), 22.3% of anti-skinning agent.

The solution obtained (solution A) has a viscosity of 3260 mPa.s. If the codimer in this solution is replaced by the same quantity by weight of mineral spirit, a solution B having a viscosity of 5540 mPa.s. is obtained.

Films of the two solutions dry, i.e. are tack free, within a few hours. The loss of volatile fractions from the codimer-containing lacquer solution A during the drying period amounts to 27.4%. By contrast, the film obtained from the comparison solution B gives off 47.5% of its weight of volatile constituents.

It follows from this that around 80% of the claimed reactive thinner remain in the film during the autoxidative drying process.

EXAMPLE 5

Production of a white lacquer 182 parts of a 55% solution of a standard commercial alkyd resin containing approximately 48% of soya oil fatty acids (Alkydal ® F 48, a product of BAYER AG) in mineral spirit/xylene (ratio by weight 84:16) are ground with 81.6 parts of titanium dioxide pigment, 3.1 parts of calcium octoate, 10 parts of a mixture of aromatic compounds and 25 parts of the codimer according to the invention. 6.7 parts of the siccative solution of Example 4, 3.8 parts of silicone oil and 3 parts of ethyl glycol acetate are stirred into the resulting mass. The solution obtained has a viscosity corresponding to a flow-out time of 81 seconds (DIN 53 211, DIN-4-cup). The white lacquer has a solids content of 69.7%.

The white lacquer dries in a few hours to form a thin-layer tack-free lacquer film.

We claim:

1. 1:1-codimers of dicyclopentadiene and 1,3-butadiene having a molecular weight of 186.
2. A process for producing the 1:1-codimers claimed in claim 1 wherein gaseous 1,3-butadiene is reacted with dicyclopentadiene in the presence of an organo-cobalt complex compound at a temperature of 40°-100° C. while introducing the major portion of the 1,3-butadiene into the reaction at a rate which does not exceed its reaction velocity.
3. The process of claim 2 wherein the reaction temperature is from 50° to 70° C.
4. The process of claim 2 wherein the pressure is from 1 to 1.5 bars.
5. The process of claim 2 wherein the 1,3-butadiene is added in a quantity of from 0.05 to 0.5 mole/h per mole of dicyclopentadiene.
6. The process of claim 2 wherein the molar ratio of 1,3-butadiene to dicyclopentadiene is from 0.1:1 to 2:1.
7. The process of claim 2 wherein the molar ratio of 1,3-butadiene to dicyclopentadiene is from 1:3 to 1:1.
8. An air-drying lacquer having a reactive thinner which is a codimer as claimed in claim 1.

* * * * *